United States Patent [19]

Amotz

[11] Patent Number: 4,665,028
[45] Date of Patent: May 12, 1987

[54] METHOD FOR PRODUCTION OF AN IMMOBILIZED ENZYME PREPARATION BY MEANS OF A CROSSLINKING AGENT

[75] Inventor: Shmuel Amotz, Mälov, Denmark

[73] Assignee: Novo Industri A/S, Denmark

[21] Appl. No.: 539,303

[22] Filed: Oct. 5, 1983

[30] Foreign Application Priority Data

Oct. 6, 1982 [DK] Denmark .............................. 4431/82

[51] Int. Cl.[4] ....................... C12N 11/00; C12N 11/14
[52] U.S. Cl. ...................................... 435/174; 435/176
[58] Field of Search .......................... 435/174, 176–182

[56] References Cited

U.S. PATENT DOCUMENTS

| | | | |
|---|---|---|---|
| 3,519,538 | 7/1970 | Messing et al. ...................... | 435/176 |
| 3,705,084 | 12/1972 | Reynolds ............................. | 435/180 |
| 3,802,909 | 4/1974 | Rockett et al. ...................... | 427/214 |
| 4,069,106 | 1/1978 | Stanley et al. ...................... | 435/177 |
| 4,116,771 | 9/1978 | Amotz et al. ....................... | 435/177 |
| 4,167,447 | 9/1979 | Masri ................................... | 435/178 |
| 4,292,199 | 9/1981 | Rohrbach et al. ............... | 435/180 X |

FOREIGN PATENT DOCUMENTS 1011671 6/1977 Canada .
1011672 6/1977 Canada .

OTHER PUBLICATIONS

Biochim. Biophys. Acta, 159 (1968), 403–405.

*Primary Examiner*—Christine M. Nucker
*Assistant Examiner*—Shawn P. Foley
*Attorney, Agent, or Firm*—Fidelman, Wolffe & Waldron

[57] ABSTRACT

A method for production of an immobilized enzyme by means of a crosslinking agent wherein the following components are brought together in aqueous medium:
 (a) an enzyme preparation;
 (b) a crosslinking agent; and
 (c) an inert water soluble salt in a relatively high concentration.

The salt hinders solubility of the enzyme in the medium, yet the enzyme is fully accessible to the crosslinking agent. High enzyme activity recovery may be obtained.

13 Claims, 9 Drawing Figures

METHOD FOR PRODUCTION OF AN IMMOBILIZED ENZYME PREPARATION BY MEANS OF A CROSSLINKING AGENT

The present invention relates to method for immobilizing enzymes and in particular to immobilization of enzymes in an aqueous reaction medium containing properly proportional levels of a dissolved inert salt and a crosslinking agent therein.

BACKGROUND OF THE INVENTION

Enzymes immobilized by means of a crosslinking agent, the art to which this invention relates, are widely employed in large quantities and a number of methods have been proposed to immobilize enzymes.

In one method, a carrier is first activated by the crosslinking agent, and then treated with the enzyme, which thus becomes firmly attached to the carrier. Such an activation may include, for example, impregnation of the carrier with a polyamine then treatment with an excess of glutaraldehyde, as is described in U.S. Pat. No. 4,292,199, or in Biotechnology and Bioengineering, 22, pp. 271-287, 1980.

Another activation and crosslinking method suggested to the art involves coating of a carrier with adsorption-promoting insoluble polymer, subsequent adsorption of the enzyme on the polymer, and further, crosslinking in situ, as is described in U.S. Pat. No. 3,705,084.

According to the method described in U.S. Pat. No. 4,069,106, a keratin-containing carrier is activated by reduction of the keratin and the enzyme is crosslinked to the keratin via S-S groups.

U.S. Pat. No. 3,802,909 suggests fracturing glass in the presence of a protein, thus providing freshly produced active sites to bind the protein. U.S. Pat. No. 3,519,538 suggests treating glass with a sequence of chemicals to produce the desired active sites. A related method for producing an immobilized enzyme is described in Biochemical and Biophysical Research Communications Vol. 36, pp. 235-242, 1969: The enzyme is adsorbed on colloidal silica, without previous activation, and then crosslinked with glutaraldehyde.

All the above mentioned methods are characterized by an attachment of a thin layer of enzyme molecules to the active sites on a carrier, and thus the amount of enzyme so immobilized is limited by the number of active sites available.

A different approach altogether, an approach to which this invention relates directly, is to place a thick enzyme containing layer on the surface of a carrier, whereby only a small fraction of the enzyme molecules is in direct contact with the carrier. This way the amount of enzyme immobilized is no longer in some direct proportion to the surface area of the carrier. The amount of enzyme bound on each carrier granule can be controlled. This approach, however, is more difficult to accomplish, as the relatively large amount of enzyme is difficult to maintain in place during immobilization. Therefore, comparatively little has been published about this approach, despite some obvious advantages for such enzyme forms. One suggestion, as described in Canadian Pat. Nos. 1,011,671 and 1,011,672, is to use an aqueous solution of a water-soluble organic solvent as the crosslinking reaction medium, the organic solvent concentration being kept high enough to keep the enzyme insoluble, yet low enough not to interfere with the crosslinking reaction. A main drawback to this method is its requirement for handling of relatively large amounts or organic solvents accompanied by explosion risks necessitating elaborate safety provisions. Also, enzyme products obtained in this way, heretofore, are believed to be deficient in physical stability and yield, which deficiencies might be due to presence of the organic solvent in the immobilization reaction medium.

Another way to obtain a thick enzyme layer is suggested in U.S. Pat. No. 4,116,771. In a limited volume of water the enzyme is treated with glutaraldehyde and an inert protein before being quickly added to the carrier, then allowed to gel, thereafter the product is granulated and finally dried. The high concentration of the crosslinking agent, which is a consequence of the limited amount of water present is often detrimental. Many enzymes are sensitive to high concentrations of crosslinking agents and reduced product yield results, because some enzyme is inactivated, or rendered inaccessible by extensive crosslinking, or both.

The difficulty facing the art's efforts to generate thick enzyme layers, on a carrier, for example, is that the reactant proportions are out of balance. To obtain low concentrations of crosslinking agent in the reaction medium, relative large quantities of reaction medium are required. However, in aqueous reaction medium, some of the enzyme dissolves before crosslinking is effective, or if already in solution, some enzyme is lost in the reaction medium, which factors suggest minimizing the volume of reaction medium. However, avoiding those losses by decreasing the volume of reaction medium would necessitate increasing concentration of the crosslinking agent and this generates the other equally serious enzyme losses already alluded to.

The approach adopted in practice of this invention is to prevent any essential part of the solid or dissolved enzyme in a solvent-free aqueous reaction medium from dissolving in or mixing with the aqueous medium, whereby the volume of reaction medium becomes less important, and low concentrations of the crosslinking reagent therein may be employed. The solubility of enzyme in the aqueous reaction medium is hindered insofar as is reasonably possible.

The object of this invention is to provide a novel enzyme immobilization process, one easy to conduct, and productive of immobilized enzymes with good physical stability.

A further object of this invention is to provide a novel enzyme immobilization process with high recovery of enzyme activity in immobilized form.

BRIEF STATEMENT OF THE INVENTION

The present method involves crosslinking an enzyme in an aqueous medium (solvent-free), which medium comprises a solution of a water soluble inert salt in concentration sufficient to hinder solubility of the enzyme in the medium. Presence of the salt prevents enzyme from being lost through solution in the medium.

It follows that the inert salts within the sense of the term "inert" are non-reactive to the enzyme, to the crosslinking agent and to any carrier materials present in the reaction mixture.

The optimum concentration of salt will depend upon the salt, and the enzyme, even on the other ingredients in the reaction mixture, such as the carrier as well as the relative proportions of salt, crosslinking agent and enzyme. However, the salt content in the aqueous medium always will exceed about 0.1M, almost always be at least 0.25M; the salt concentration range may extend to saturation. The preferred concentration range for the salt is 0.5M–3M.

Although immobilization of enzymes on carriers is preferred practice of this invention, the principles and practices of this invention include immobilization of enzymes without a carrier being present.

GENERAL DISCUSSION OF THE INVENTION

Thus, the method of this invention comprises bringing together the following components in a solvent-free aqueous medium:

(a) an enzyme preparation;
(b) a crosslinking agent; and,
(c) a water soluble inert salt, namely a salt which does not react with the crosslinking agent or inactivate the enzyme, in concentration sufficient to hinder solubility of the enzyme in the reaction medium. The reduced solubility reduces dissolution loss of enzyme if the enzyme is introduced in solid state form. If dissolved enzyme is introduced, the hindered solubility prevents loss into the reaction medium;
(d) optionally, carrier materials, such as carrier particles on which the enzyme is to be coated.

Use of a solvent-free aqueous medium crosslinking system is advantageous for avoiding explosion risks, solvent costs and solvents recovery expenses. If excess crosslinking agent is employed, the excess may be removed by water washing the immobilized enzyme.

It is to be understood that solid form enzyme preparations to be crosslinked and immobilized by practice of this invention may be a solid enzyme of high purity, or a solid form enzyme preparation which contains inert additives, e.g., fillers, reinforcing agents, binders or granulating agents, or a dissolved enzyme preparation. Enzyme in solution also may be crosslinked and immobilized by practice of this invention, and such is contemplated.

It should be understood that one or more enzymes, one or more crosslinking agents, and one or more salts may be used in the method of this invention. Also, it should be understood that the sequence in which the above described components are brought together in the aqueous reaction medium is arbitrary, except, however, if the enzyme and crosslinking agent are brought together in aqueous medium before addition thereto of the water soluble inert salt, enzyme yield will decrease if the salt addition is delayed. It goes without saying that when some particular order of addition or mixing sequence produces the better results, it is to be preferred.

Although the method of this invention may be practiced without immobilizing the enzyme on a carrier, a carrier is usually part of immobilized enzyme products preferred by the art, because of the possibility offered by the carrier for producing an enzyme granule with flow properties suited to packed bed operations. In preferred embodiments of the method according to the invention the immobilized enzyme product made comprises a carrier coated with a thick enzyme containing layer. Enzyme loading may be controlled by variation in thickness of the enzyme containing layer.

Practice of this invention is applicable to all enzyme forms. Either solid state enzyme preparations or dissolved enzymes can be coated on the surface of a carrier in high activity yield by practice of this invention. If the enzyme to be immobilized is in dissolved form, impregnating the carrier with the enzyme solution prior to adding the crosslinking agent is preferred in the reactant addition sequence. Thus, the enzyme to be immobilized may be intracellular or extracellular, in solid form or in solution. The form, purity and concentration of the enzyme are matters of choice.

In addition, immobilization according to practice of this invention is applicable to most, if not all enzymes. In preferred embodiments of the invention, the enzyme is chosen from the group consisting of glucose isomerase, amylases, in particular amyloglucosidase, pullulanase, lactase, pectinases, naringinase, penicillin acylases, inulinases, lipases, and proteases.

Any crosslinking agent heretofore employed in aqueous medium crosslinking of enzymes may be used for practice of this invention. However, for greater understanding of this invention, the discussion of the crosslinking agent which follows will be keyed to glutaraldehyde, the preferred crosslinking agent.

Thus, in preferred embodiments of the method according to the invention, the crosslinking agent is glutaraldehyde. Glutaraldehyde is a relatively cheap, very effective and yet mild crosslinking agent that is not objected to by health authorities.

Preferably, the glutaraldehyde concentration in the aqueous reaction medium is between 0.001 and 5% weight by volume (w/v), preferably from 0.005 to 1% w/v. As is demonstrated in the Examples herein, the enzyme recovery depends on the concentration of glutaraldehyde, and usually, the glutaraldehyde concentration corresponding to a maximum enzyme recovery will be in the above indicated preferred ranges. The percentage w/v is calculated by the formula:

$$\frac{\text{weight of glutaraldehyde, g}}{\text{volume of salt solution and glutaraldehyde, ml}} \times 100 = \% \, w/v$$

For best results in crosslinking a particular enzyme, cut and try tests at various concentrations of crosslinking reagent and the dissolved salt are advisable to select optimum process conditions for the immobilization. Considerable flexibility exists in the process since reasonably optimal results are obtained within a concentration band wherein said concentration relates generally inversely to glutaraldehyde concentration in the reaction medium. With high salt concentrations, the optimum crosslinking agent concentrations are near the lowest end of the above given range. Crosslinking agent concentrations at the high end of the above given range generate optimum results with low salt concentration. The inverse relationship allows concentration of crosslinking agent to be pre-selected to a level which would cause minimal damage to the enzyme, yet, impart good stability, and cut and try tests used to ascertain an appropriate salt concentration for optimum recovery of enzyme activity.

For all practical purposes, presence of one or more inert salts dissolved in the aqueous crosslinking medium renders the enzyme, insoluble in the aqueous medium, while keeping it fully accessible to the crosslinking agent, allowing use of the relatively low preferred 0.005–1% w/v concentration for the crosslinking agent. This concentration range for glutaraldehyde has been found to cause minimal loss of enzyme activity, yet impart sufficiently good stability to the immobilized enzyme product. Moreover, little, if any, enzyme is lost in the spent reaction medium.

THE SALTS

Since the rationale for presence of the water soluble inert salt dissolved in the aqueous crosslinking reaction medium is primary physical for hindering solubility of the enzyme in the reaction medium the salts are required to be non-reactive to the enzyme, to the crosslinking agent, and to any carrier material or materials present, i.e., be inert and water soluble. Eliminated then from practice of this invention are, therefore, water soluble salts which react with the enzyme; for example, the silver or mercury salts which commonly inactivate enzymes, and water soluble salts which react with the crosslinking agent e.g., with glutaraldehyde such as, for example, ammonium salts (except for quarternary ammonium salts) and sulfites.

A great number of water soluble salts are, however, inert, and, therefore, suitable for practice of this invention. Indeed, a large number of salts may be named as preferred for practice of this invention.

In preferred embodiments of the invention, the salt is chosen from the group consisting of sulfate, phosphate, citrate, bicarbonate, carbonate, fluoride, acetate, tartrate, polysulfate, polyphosphate, ferrocyanide, phenolsulfonate, sorbate, ethylsulfate, chloride, nitrate and succinate of quarternary ammonium or one of the alkali metals; particularly preferred are sodium sulfate, sodium phosphate, potassium phosphate, and potassium citrate. Generally, the above named preferred salts are cheap and recoverable; their use permits production of immobilized enzyme forms with high enzyme activity recovery.

The salt concentration in the aqueous reaction medium is between 0.1M (Molar) and saturation, preferably from about 0.5M to about 3M.

As appears from the Examples later in this specification it is possible to choose a glutaraldehyde concentration and a salt molarity inside the above indicated intervals, which correspond to a very high enzyme activity recovery. Peak enzyme recovery appears to be attributable to the combined concentrations of glutaraldehyde and the salt in a band so to speak over the interval of the preferred range for each ingedient, one at a time, but not both together. However, peak enzyme activity recovery occurs over a narrow interval of crosslinking agent concentrations for a given salt concentration, and, sometimes, over a narrow interval of salt concentration for a given crosslinking agent concentration. To repeat, the optimum concentrations are inversely related, low crosslinking agent concentration going with high salt concentration and high crosslinking agent with low salt within the preferred ranges of 0.5M-3M for the salt and 0.005 to 1% w/v for the crosslinking agent.

It has been found also that the water soluble inert salts suited to practice of this invention vary greatly, salt to salt, with regard to their effectiveness, and, furthermore, effectiveness of a particular salt may vary from one enzyme to another. Different salts in the above listed preferred salts may be most effective for each combination of enzyme and crosslinking agent.

The considerable number of water soluble salts that satisfy the water solubility and non-reactivity requirements adds additional flexibility to practice of this invention. The salts or salts may be selected for whatever reasons make presence of one salt or another modestly more advantagous for immobilizng a particular enzyme with a particular crosslinking reagent on a given carrier or for reasons extrinsic to practice of this invention, such as a salt easier to recover and recycle, or the less expensive.

Some broad guidelines with regard to the choice of particular salts can be provided. It is advisable to choose the more soluble salt when two salts otherwise seem to be equivalent. Thus, $Na_2SO_4$ is usually to be preferred over $K_2SO_4$, because of the much higher solubility. It has also been found that, in general, salts of multivalent anions, such as sulfates, phosphates, carbonates, citrates and the like, are more effective for practice of this invention than the monovalent anions, such as chlorides and nitrates. The reverse, however, usually is ture for the cations. The monovalent cations, such as $Na^+$, $K^+$ or tetramethylammonium, are more effective than the multivalent cations such as $Mg^{++}$ or $Ca^{++}$. The most preferred salts for practice of this invention correspond to the above guidelines, e.g., alkali metal salts of sulfates, phosphates and citrates. In particular, sodium sulfate, sodium phosphate, potassium phosphate, potassium citrate and tetramethylammonium sulfate are the preferred salts.

Thus, to recapitulate, practice of this invention allows a wide choice of water soluble inert salts for selecting a particular salt productive of best results in one or more aspects of the immobilized enzyme product or of the immobilization process. Then a choice is available within the optimal band of salt and crosslinking agent concentrations. Moreover, since both product characteristics and the immobilization process are often less sensitive to independent changes in salt concentration than to independent changes in concentration of the crosslinking agent, some independent variations can be made in salt concentration for a given crosslinking agent concentration. However, absent reason for using more of the salt than is needed at any given concentration of crosslinking agent, the least effective salt concentration might well be the usual concentration selected.

Another advantage of including inert, water soluble salts in the aqueous crosslinking medium that has been discovered is that presence of salts seems to prevent the solid state form enzymes from aggregating during the immobilization reaction. Such aggregation is undesirable as it results in reduced efficiency for the immobilization reaction and in enzyme coated granules which exhibit inferior liquid flow properties during their employment. In this regard, individual salts differ widely.

THE METHOD

The method of the invention may be carried out as a number of steps in any order.

In one preferred embodiment of the invention, a carrier is first treated with an enzyme solution, dried and then treated in an aqueous solution of the crosslinking agent and salt, thereafter washed and optionally dried. In variations of the same process, the salt may be included in the enzyme solution, or a salt solution may be added separately to the carrier, either before or after treatment with the enzyme. In yet another embodiment of the invention, the enzyme is treated first with the crosslinking agent and immediately afterwards with the salt.

The carrier may be avoided altogether, and the enzyme treated in a coagulating bath with the crosslinking agent and the salt. Thus, the enzyme may be dissolved then coagulated in a salt bath, the crosslinking agent being added to the enzyme solution or to the salt bath, before or after coagulation. Also, the salt may be added to the reaction medium as a dry powder, instead of in solution, to limit the total amount of water in the system.

Thus, the order in which the different components are brought together, or their initial state, that is, whether in solution or dry, is not critical for the method of the invention. The process details actually selected for any particular embodiment of this invention will depend upon characteristics sought in the immobilized enzyme product. For example, to form lightweight fibrous enzymes, little or no carrier is used and the coagulating bath technique described above is employed.

As is well known to the art, the pH, temperature and duration of the crosslinking reaction may have a profound effect on the recovery of enzyme activity in an immobilized enzyme, depending also on the enzyme and any inert additives present. In general, it has been found that a pH range from about 4 to about 9 is suitable. The temperature range suitable for most immobilization reactions is from about 15° C. to about 30° C., though higher temperatures may be used with advantage in certain cases, e.g., when it is desired to shorten the duration of the crosslinking reaction, and lower temperatures may be used with advantage in case of very temperature sensitive enzymes. The duration of the crosslinking reaction may vary widely, from a few minutes to a few days, depending on pH and temperature as well as the type and concentration of the crosslinking agent, the type and concentration of the salt, and the enzyme being immobilized. For immobilizing with glutaraldehyde as the crosslinking agent, treatment of from about ten minutes to several hours at room temperature, at pH in the range of pH 4–9 appears to be suitable.

For further understanding of this invention reference is made to the hereto attached drawing wherein.

Figure 6:
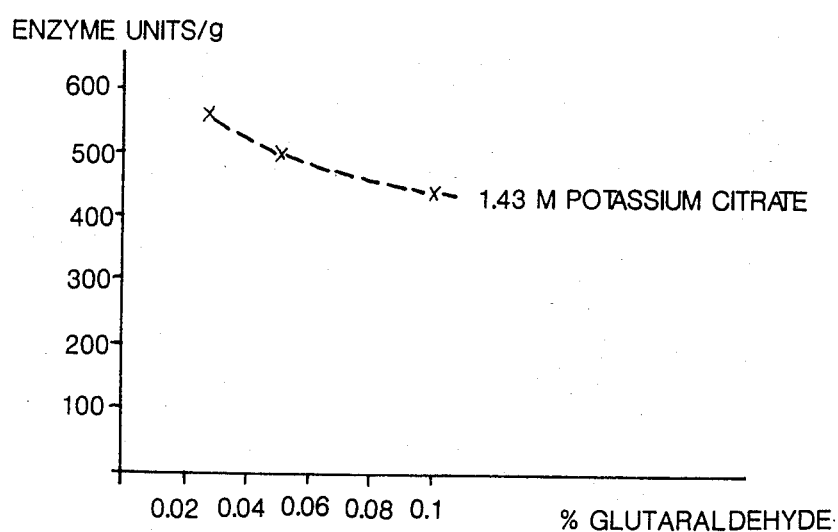
Figure 7:
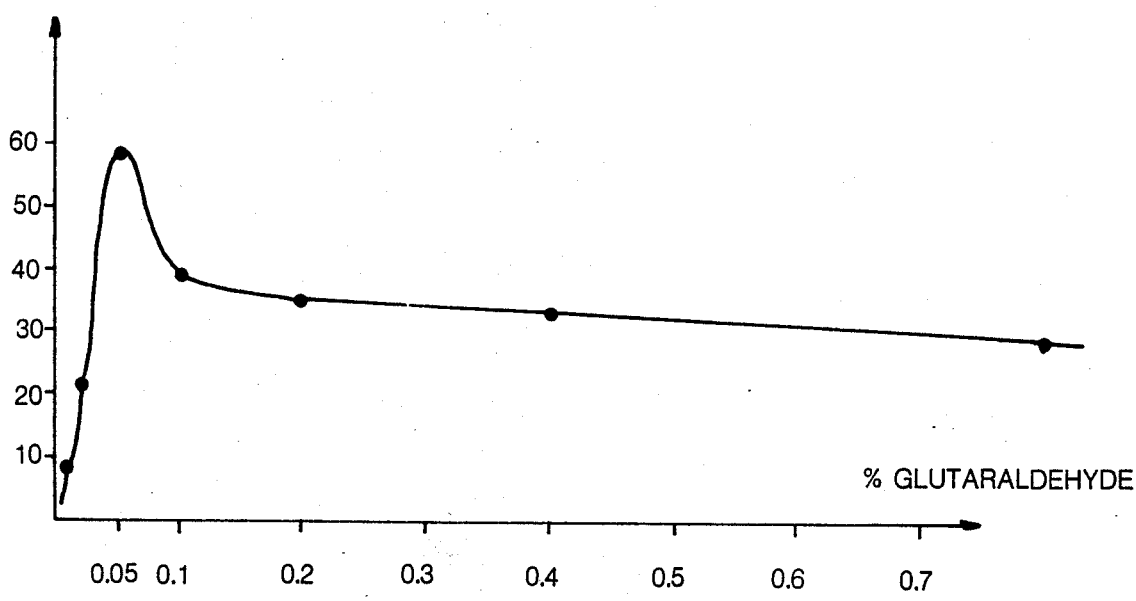
Figure 8:
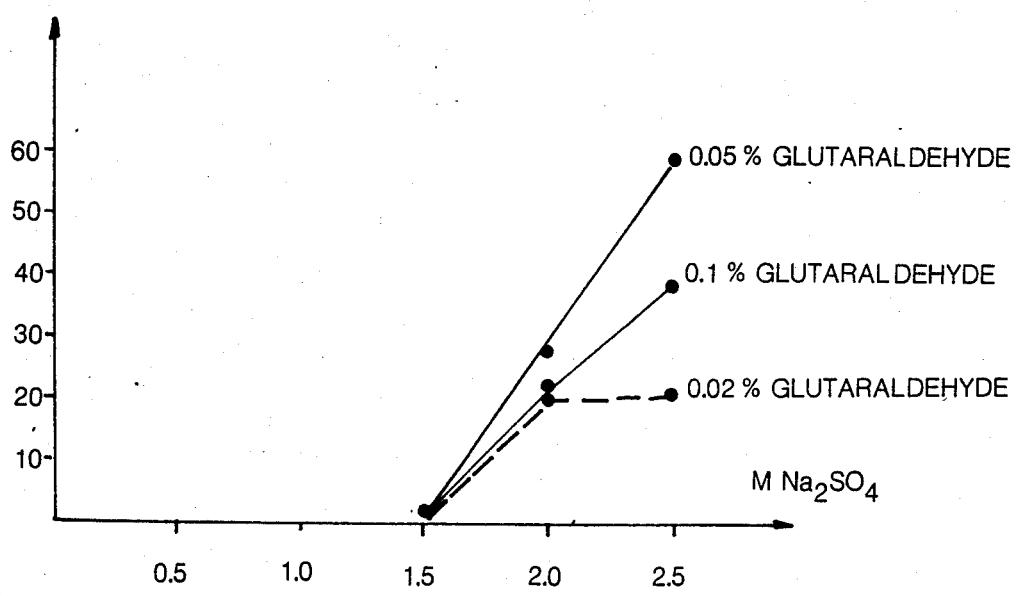
Figure 9:
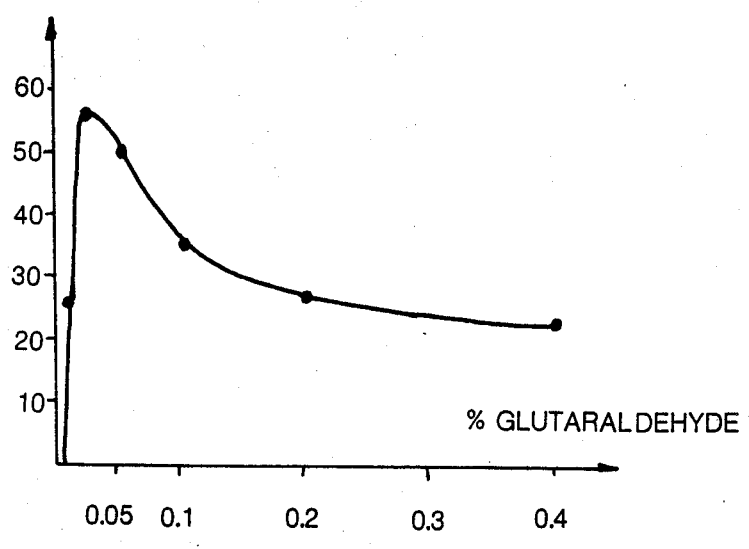

FIG. is a graph of the enzyme activity recovery against potassium phosphate concentration for the enzyme products made according to the Example 5 hereinafter;

FIG. 6 is a graph of the enzyme activity recovery against glutaraldehyde concentration for the enzyme products made according to the Example 6 hereinafter;

FIG. 7 is a graph of the enzyme activity recovery against glutaraldehyde concentration for the enzyme products made according to the Example 12 hereinafter;

FIG. 8 is a graph of the enzyme activity recovery at various glutaraldehyde concentrations against molarity of $Na_2SO_4$ for the enzyme products made according to the Example 13 hereinafter; and FIG. 9 is a graph of the enzyme activity recovery against glutaraldehyde concentration for the enzyme products made according to the Example 14 hereinafter.

The method of the invention is illustrated by the following examples of preferred modes thereof. Exemplified hereinafter is how the method hereof applies to preparation of an immobilized glucose isomerase, an immobilized lactase, and an immobilized amyloglucosidase.

One best mode of this invention exemplified hereinafter involves use of the method hereof in formation of the enzyme coated carrier granules described by copending application, Ser. No. 539,305, filed concurrently herewith and now U.S. Pat. No. 4,572,897.

In the following, reference is made to different NOVO literature references. Copies of all these references can be obtained from NOVO INDUSTRI A/S, Novo Alle, DK-2880 Bagsvaerd, Denmark.

EXAMPLE 1

1.4 kg cellulose fiber, type Arbocel BC 200, 5.6 kg Clarcel Celite (diatomaceous earth) and 8 kg 20% w/w gelatine Bloom 200 solution, all at 60° C., were mixed in a plow-share type mixer and the thick mass so obtained was extruded by an extruder equipped with a 1.5 mm screen and then spheronized in a Marumerizer, as described in U.S. Pat. No. 3,277,520. The extruder was of the twin screw type model EXDC-100, and the spheronizer model was Q-400.

The particles thus obtained were dried in a fluid bed tower and sieved, and the fraction 1.2–2.0 mm collected, with the residue recycled. The particle fraction 1.2–2.0 mm was then treated for three hours at room temperature with 3.6 kg 50% w/v glutaraldehyde solution, removed from the solution, and thoroughly washed with de-ionized water, then dried.

4.5 kg of the dried carrier particles were fluidized in a pilot-plant type fluid bed apparatus, and 9.3 kg solution of 19% w/w partly purified glucose isomerase from *Bacillus coagulans* NRRL 5650 (activity 3240 units/g dry matter, the activity unit being defined in NOVO analyseforskrift AF 189/1), was sprayed onto the particles at 50°–55° C., and the particles were allowed to dry. The product thus obtained contained 28% by weight of partially purified glucose isomerase dry matter with 85% recovery of the activity.

Figure 1:
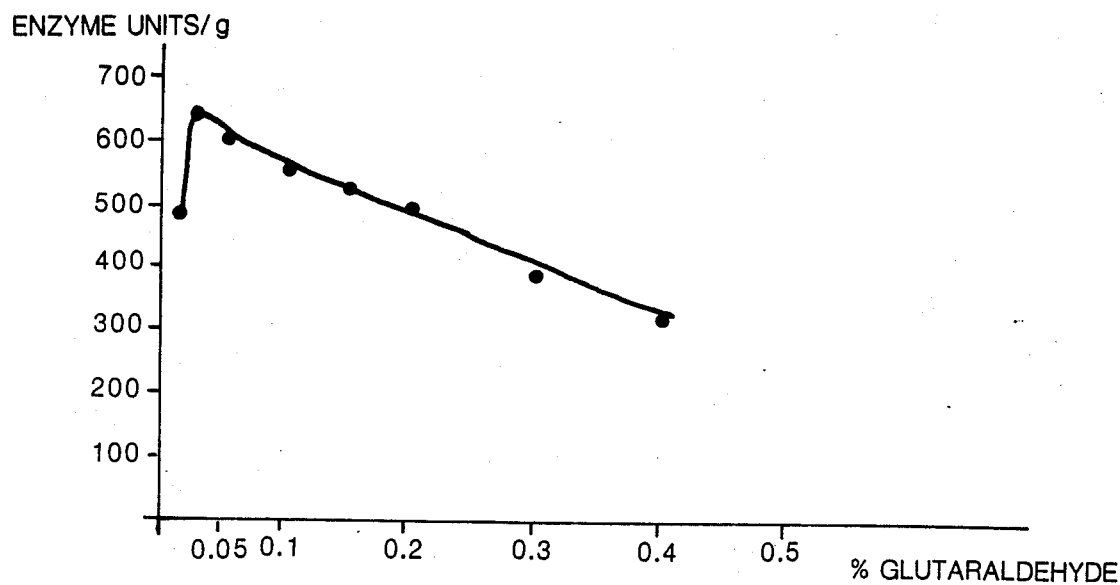
FIG. 1 is a graph of the enzyme activity recovery against glutaraldehyde concentration of the enzyme products made according to the Example 1 hereinafter.

Portions of 20 g of the dry carrier particles coated with partially purified glucose isomerase preparation to the extent of 28% w/w were suspended and gently stirred at room temperature in 500 ml solution containing 0.06M sodium phosphate, 1.4M $Na_2SO_4$ and different amounts of glutaraldehyde, adjusted to pH 7.0. After one hour, the particles were removed and suspended for one hour in 0.06M sodium phosphate solution adjusted to pH 7.0. This washing was repeated three times, and then the particles were left overnight in the phosphate solution, whereafter their activity was determined according to NOVO analyseforskrift AF 189/1. The results are shown in FIG. 1, which is a graph, where percentage of glutaraldehyde is plotted against enzyme activity recovery expressed in enzyme units/g. The high degree of sensitivity of enzyme recovery to glutaraldehyde concentration can be seen in the results plotted in FIG. 1.

EXAMPLE 2 (Comparison)

Figure 2:
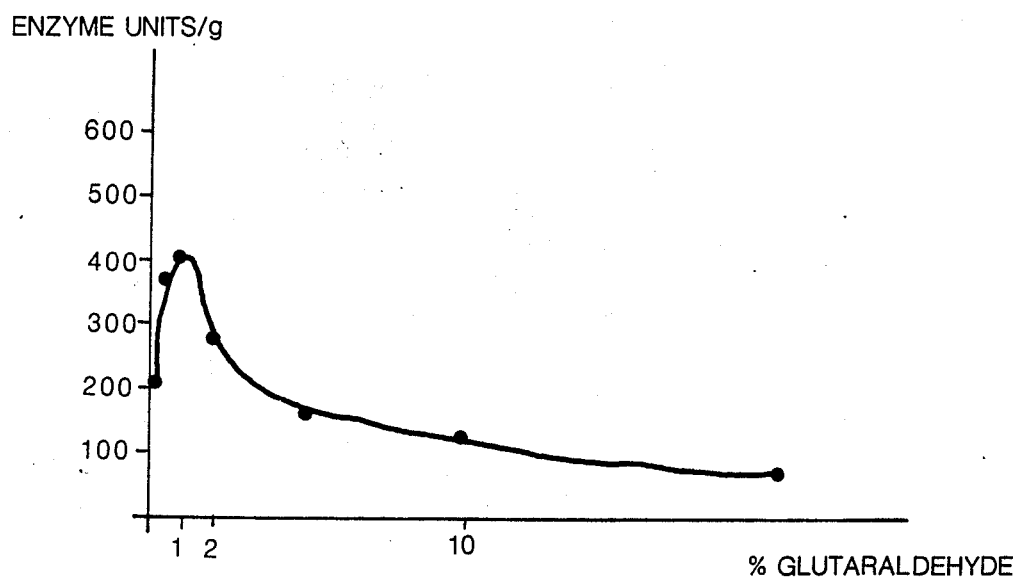
FIG. 2 is a graph of the enzyme activity recovery against glutaraldehyde concentration for the enzyme products made according to the Example 2 hereinafter.

Enzyme coated particles were prepared as in Example 1, only no salt was added, apart from the minimal amount of phosphate buffer (0.06M sodium phosphate, pH 6.5). The percentage of glutaraldehyde employed was plotted against the enzyme recovery in units/g, vide FIG. 2, which shows that the crosslinking agent has contradictory effects. The optimum enzyme recovery is established, in this case, at around 1% glutaraldehyde. From a comparison between FIGS. 1 and 2 it appears that the optimum glutaraldehyde concentration is approximately 40 times as high as when 1.4M sodium sulfate is present, and that the yield is only about 60% of the yield with the salt.

EXAMPLE 3

Figure 3:
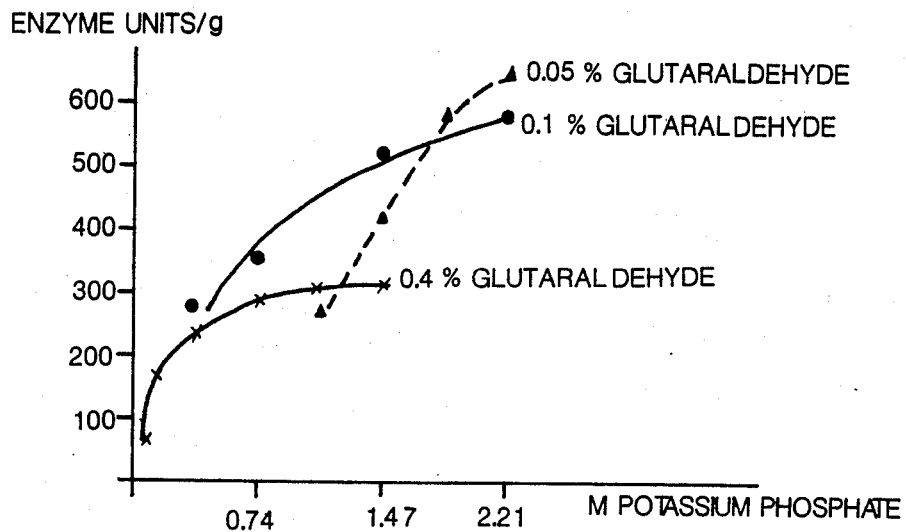
FIG. 3 is a graph of the enzyme activity recovery against potassium phosphate concentration for the enzyme products made according to the Example 3 hereinafter.

Particles were prepared as in Example 1, only in this case, potassium phosphate was used as the salt, and the salt concentration was varied while keeping the glutaraldehyde concentration constant and the pH at 6.5. The percentage of potassium phosphate was plotted against the enzyme recovery in units/g, vide FIG. 3, from which the beneficial effect of increasing the salt concentration clearly appears, especially at a low glutaraldehyde concentration.

EXAMPLE 4

The experiment in Example 3 was repeated, only here sodium sulfate was used instead of potassium phosphate. The molarity of $Na_2SO_4$, was plotted against the enzyme recovery in units/g, vide FIG. 4, from which the beneficial effect of the salt clearly appears. As it also appears from FIG. 4, an optimum for the salt effect exists, beyond which the activity recovery decreases, whereby this optimum depends on the glutaraldehyde concentration.

EXAMPLE 5

Figure 4:
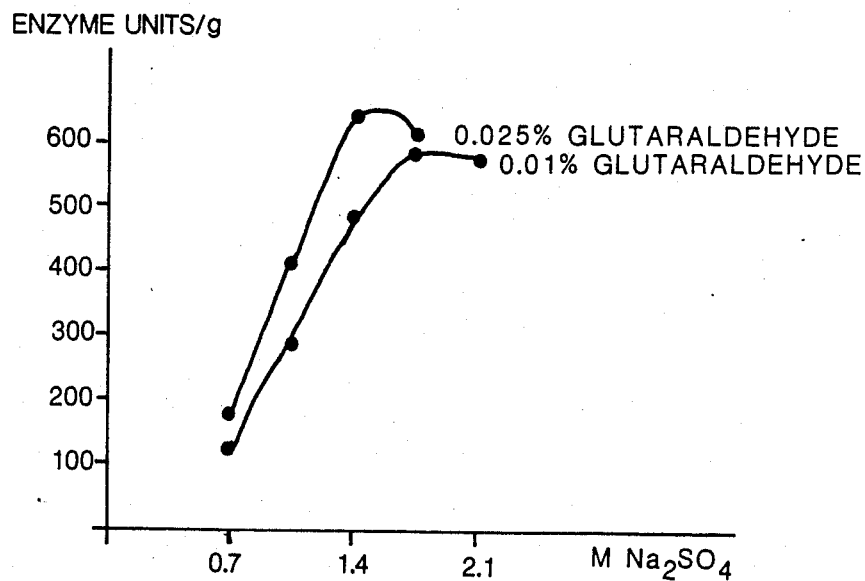
FIG. 4 is a graph of the enzyme activity recovery against sodium sulphate concentration for the enzyme products made according to the Example 4 hereinafter.
Figure 5:
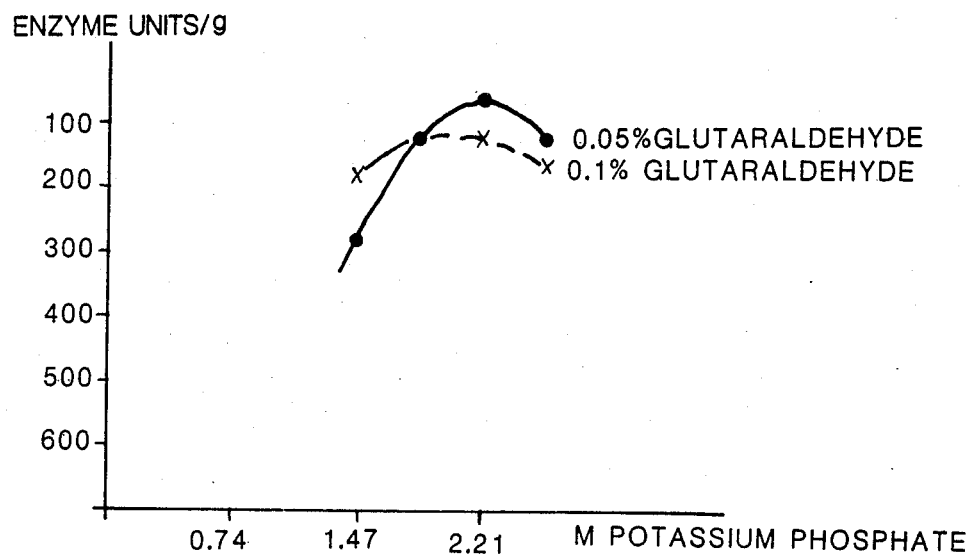

The experiment described in Example 3 is repeated, only the salt concentration was increased. The molarity of potassium phosphate was plotted against the enzyme recovery in units/g, vide FIG. 5. A comparison between FIGS. 4 and 5 shows that $Na_2SO_4$, and potassium phosphate behave similarly.

EXAMPLE 6

The experiment described in Example 1 was repeated, only potassium citrate pH 7.0 was used instead of phosphate and sulfate in the crosslinking medium. In FIG. 6 the glutaraldehyde concentration is plotted against the activity in enzyme units/g, and the results clearly resemble those in Example 1.

EXAMPLE 7

20 g of dried carrier particles produced as described in Example 1 were fluidized in a Lab type fluid bed. 45.8 g of 11.0% w/w homogenized cell sludge (fermented as indicated in Example 1 of Danish Patent Application No. 5190/79, sludge produced as indicated in Example 4 of Danish Patent Application No. 5190/79) containing 80.1 U/g of thermophilic lactase from Bacillus sp. NRRL B-11.229 were sprayed onto the carrier particles at 30°–40° C., and the coated particles were allowed to dry.

The lactase activity unit is defined as that amount of lactase, which will split 1 μmol of lactose/minute under the following reaction conditions: Substrate concentration=10% lactose, temperature 60° C., pH=6.5 and reaction time=30 minutes. The activity recovery was 79.8%.

10 g coated spheres were then treated in 250 ml solution containing 0.06M $Na_2HPO_4$, 1.4M $Na_2SO_4$ and 0.1% w/v glutaraldehyde at pH 7.5. After one hour at room temperature the particles were removed and washed thoroughly with 0.06M $K_2HPO_4$ at pH=7.5. The activity recovery was 17.2%.

EXAMPLE 8

24 g of dried carrier particles produced as described in Example 1 were soaked in 20.2 g solution of a 39.6% w/w partly purified amyloglucosidase from Aspergillus niger produced by ultrafiltration of the commercial product AMG 200 L (described in NOVO brochure NOVO Enzymes AMB, B 020 g-GB) in order to remove low molecular constituents to a dry matter content of 39.6% w/w (activity 2610 IAG/g, the activity unit being defined in NOVO Analyseforskrift AF 159/2). Vacuum was applied for one hour. The product thus obtained contained 25% by weight of enzyme dry matter with 77.9% activity recovery.

20 g particles with 71.8% dry matter were then treated in 1600 ml of a solution of 0.06M $NaH_2PO_4$, 1.4M $Na_2SO_4$ and 0.2% glutaraldehyde at pH=4.5. After one hour the particles were removed by filtration and washed with 0.6M $NaH_2PO_4$ at pH=4.5. Enzyme activity recovery was 55.1%.

EXAMPLE 9

40 g carrier particles prepared as described in Example 1 with a dry substance content of 98.8% and 24 g vacuum evaporated partially purified Bacillus coagulans glucose isomerase concentrate with 5% glucose and 8% sodium sulphate added (dry substance 41.8%) was mixed and the liquid was allowed to exchange the air in the pores of the particles by vacuum treatment. Weight after mixing was 63.22 g. Dry substance was 79.2%.

18 g portions of this preparation (∼14 g dry substance) were treated for one hour at room temperature with 375 ml of a solution containing 0.1, 0.2 or 0.3% glutaraldehyde, and in all cases, 1.5M sodium sulphate, 5% glucose, and 0.6M sodium phosphate, adjusted to pH 7.5.

After this treatment, the portions were washed five times with approximately 150 ml 1% sodium phosphate, pH 7.5.

The enzyme activity was determined according to AF 189/1 after draining of the liquid from the particles. Also dry substance was determined on the drained particles. The test results are tabulated below.

|  | % dry substances | U/g wet | U/g dry | Yield, % | Immob. yield, % |
| --- | --- | --- | --- | --- | --- |
| Enzyme concentrate | 41.8 | 1415 | 3385 | — | — |
| Enzyme concentrate + carrier | 79.2 | 463 | 585 | 86 | — |
| Immob. with 0.1% GA | 32.5 | 158 | 486 | 72 | 83 |
| Immob. with 0.2% GA | 38.9 | 141 | 362 | 53 | 62 |
| Immob. with 0.3% GA | — | 117 | 333 | 49 | 57 |

Portions equivalent to 5 g dry substance were tested for pressure drop.

| Glutaraldehyde concentration at immobilization | Pressure drop | |
| --- | --- | --- |
|  | 25 hours | 50 hours |
| 0.1% | 3 | 5 |
| 0.2% | 1 | 3 |
| 0.3% | 2 | 3 |

EXAMPLE 10

This Example describes a method for producing an immobilized enzyme product based on activated carbon from Norit as a carrier.

Thus, 20 g of Norit Rox 0.8 activated carbon, type A-3397 were soaked in 33 g solution of 39.2% w/w partly purified glucose isomerase from *Bacillus coagulans* (activity 3950 U/g, the activity unit being defined in NOVO "Analyseforskrift" AF 189/1).

Vacuum was applied for 20 h at 4° C. except that vacuum was released four times during this period. The product thus obtained contained 35% by weight of partially purified glucose isomerase dry matter with 97% recovery of activity.

98% of the above indicated, aggregate product was then immobilized in 890 ml of a solution of 0.06M $KH_2PO_4$, 1.4M $Na_2SO_4$ and 0.18% gluaraldehyde, adjusted to pH 7.5 with 4N NaOH.

After two hours at room temperature with gentle agitation, the particles were removed by filtration and washed thoroughly with 0.06M $KH_2PO_4$, pH 8.0. Recovery of activity was 31%.

EXAMPLE 11

This example describes a method for producing an immobilized enzyme preparation with a carrier consisting of silica spheres with a diameter of approximately 2 mm.

A. 20 g of the silica spheres were fluidized in a lab type fluid bed, and 40 g solution of 15% w/w partly purified glucose isomerase from *Bacillus coagulans* (activity 3306 U/g dry matter, the activity being defined in NOVO analyseforskrift AF 189/1) were sprayed onto the spheres at 25°–30° C., and the coated spheres were allowed to dry. The product thus obtained contained 23% by weight of partially purified glucose isomerase with 78% recovery of activity.

95% of the coated spheres was then treated in 500 ml solution containing 0.06M $K_2HPO_4$, 1.4M $Na_2SO_4$ and 0.1% w/v glutaraldehyde, adjusted to pH 7.5 with 4N NaOH; after one hour at room temperature the particles were removed and washed thoroughly with 0.06M $KH_2PO_4$ at pH 8.0. Then the activity was determined.

The activity recovery in regard to the crosslinking step was 55%.

B. 20 g of the silica spheres were soaked in 15 g solution of 40% w/w partly purified glucose isomerase from *Bacillus coagulans* (activity 3270 U/g dry matter) with 0.56M $Na_2SO_4$ added. Vacuum was applied for 20 minutes except that vacuum was released 4 times during this period. The product thus obtained contained 20% by weight of partially purified glucose isomerase with 90% enzyme activity recovery. 95% of the coated spheres was then treated as described in part A of this example.

The activity recovery in regard to the crosslinking step was 45%.

In some cases where the enzyme is particularly difficult to crosslink, salts may become not only advantageous but rather indispensible if the enzyme has to be immobilized in a pure state. A good example is the amyloglucosidase, which is produced by NOVO (and sold e.g. under the trade mark AMG 200 L, vide the brochure NOVO enzymes AMG, B B 020 g-GB 2500 July 1982 which is practically impossible to immobilize with glutaraldehyde when in a pure state: it has been found impossible to insolubilize this amyloglucosidase even at as high a concentration as 50% w/w glutaraldehyde. However, by means of the salts used in the method according to the invention (though at rather high concentrations) it is possible to effectively insolubilize the enzyme even at as low a concentration as 0.05% w/v glutaraldehyde, as demonstrated by the following examples 12–17. The thus obtained preparations, which have excellent filterability and yet can be easily floated, may be used with advantage in the production of low calorie beer, for example.

EXAMPLE 12

Commercial NOVO AMG 200 L diluted to a dry substance content of 30% w/v was mixed with Hyflo Celite and dried, whereby a preparation containing 21% w/w dry matter originating from the AMG preparation was obtained. 1 g portions of the preparation were then added to a solution containing 2.4M $Na_2SO_4$, 0.06M potassium phosphate at pH 6.5 and glutaraldehyde at different concentrations at 32° C., and the entire mixture was left at that temperature for 20 hours. The particles were then filtered andd rinsed three times with de-ionized water, and the activity yield measured. The results show the familiar pattern of the two opposite effects of glutaraldehyde with an optimum at 0.05%, vide FIG. 7.

EXAMPLE 13

The same procedure as in example 12 was repeated, only here different concentrations of $Na_2SO_4$ were used. The activity recovery with this enzyme is extremely sensitive to the amount of salt present, vide FIG. 8.

EXAMPLE 14

The procedure in example 12 was repeated, except that here an AMG preparation containing only half as much enzyme was used. As a result a shift of the glutaraldehyde optimum to a lower concentration was clearly observed, vide FIG. 9.

EXAMPLE 15

NOVO AMG 200 L was spray-dried, and the resulting powder was used as a starting material, and the procedure was varied somewhat: 0.5 g of the AMG powder was added to 100 ml of a solution containing 2.5M $Na_2SO_4$, 0.1M potassium phosphate, pH 6.5, and 1% w/v glutaraldehyde at 32° C., and held at that temperature for 1 hour with occasional shaking. The insoluble particles thus formed were then filtered and incubated again in the same medium, only without glutaraldehyde, and at the same temperature for further 20 hours. They they were filtered and rinsed three times with de-ionized water. These easily-filtering microspheres had a diameter of about 10–100 μm, and retained 19% of the original activity.

EXAMPLE 16

A procedure identical to that of example 15 was here followed except that the glutaraldehyde was added to the salt solution after the enzyme powder had been added to it. A similar product with 34% of the original activity was thus produced.

EXAMPLE 17

Again the procedure in example 15 was followed, except that only 0.4% w/v glutaraldehyde was used and the total incubation was shortened to 3 hours. A product with 37% of the original activity was thus produced.

EXAMPLE 18

This example illustrates the applicability of the method according to the invention with other crosslinking agents than glutaraldehyde, namely multivalent cations. In this case $Sn^{++++}$ was used as the crosslinking agent. Thus, 0.5 g of the Celite-AMG preparation from example 12, in the state before crosslinking was added slowly and with stirring to a 100 ml solution containing 2M $Na_2SO_4$, 0.4M potassium acetate (pH 4.35) and 0.0086M $SnCl_4$, $5H_2O$, and the mixture was left at room temperature for 5 minutes with occasional shaking. The particles thus formed were filtered and dispensed in 100 ml 0.2M potassium acetate, pH 4.35, and the suspension stirred for 5 minutes. This procedure was repeated 3 times. The end product had an enzyme activity recovery of 43%.

EXAMPLE 19

In this example a product was made according to the method described in example 18 only the acetate and the stannic salt concentrations were double to 0.8M and 0.017M, respectively. A similar product was obtained, the enzyme activity recovery being 65%.

EXAMPLE 20

In this example also the procedure in example 18 was repeated only the acetate concentration was reduced to half, i.e. 0.2M. Again a similar product was obtained, with an enzyme activity recovery of 48%.

EXAMPLE 21

In this example the use of yet another crosslinking agent, namely benzoquinone, is described. Thus 0.5 g of a dried Celite-AMG preparation as in example 12 was added to 75 ml of a mixture containing 2.1M $Na_2SO_4$ and 0.05M sodium acetate, and then 5 ml of a solution of 20% w/v of benzoquinone in pure ethanol was added, and the whole mixture was left alone at room temperature for 80 minutes, with occasional stirring. The particles thus formed were then filtered, dispersed in 75 ml 0.1M potassium acetate buffer, pH 4.4, stirred for 5 minutes and re-filtered. This procedure was repeated three times, and then the activity was determined. The enzyme activity recovery was 14%.

I claim:

1. A method for production of an immobilized enzyme by means of a crosslinking agent, which comprises bringing together the following components in an aqueous medium:

(a) an enzyme preparation, (b) a water soluble crosslinking agent, and (c) a water soluble inert salt other than an ammonium salt in concentration exceeding 0.1M sufficiently to hinder the solubility of the enzyme in said aqueous medium whereby crosslinking of said enzyme takes place, whereafter the immobilized solid form enzyme is recovered, the salt being inert to the enzyme and to the crosslinking agent.

2. A method according to claim 1 wherein a carrier is also present in said aqueous medium, the salt being inert to the carrier.

3. A method according to claim 2 wherein the enzyme preparation comprises said carrier coated with a layer of solid enzyme.

4. A method according to claim 2 wherein the enzyme preparation comprises a porous carrier impregnated with an enzyme solution.

5. A method according to claim 1 wherein the crosslinking agent comprises glutaraldehyde.

6. A method according to claim 5 wherein the glutaraldehyde concentration in the aqueous medium is between 0.001 and 5% w/v.

7. A method according to claim 1 wherein the salt is selected from the group consisting of a sulfate, phosphate, citrate, bicarbonate, carbonate, fluoride, acetate, tartrate, polysulfate, polyphosphate, ferrocyanide, phenolsulfonate, sorbate, ethylsulfate, chloride, nitrate and succinate of an alkali metal.

8. A method according to claim 7 wherein the salt is selected from the group consisting of sodium sulfate, sodium phosphate, potassium phosphate, and potassium citrate.

9. A method according to claim 1 wherein the salt is tetramethylammonium sulfate.

10. A method according to claim 1 wherein the salt concentration is between 0.2M and saturation.

11. A method according to claim 1 wherein the enzyme is selected from the group consisting of glucose isomerase, amylases, pullulanase, lactase, pectinases, naringinase, penicillin acylases, inulinases, lipases, and proteases.

12. A method according to claim 11 wherein the enzyme is selected from the group consisting of glucose isomerase and amyloglucosidase.

13. A method according to claim 1 wherein the crosslinking agent comprises glutaraldehyde in concentration of 0.005–1% w/v and wherein salt concentration is 0.5M–3M with salt concentrations and glutaraldehyde concentrations being inversely related, such that higher salt concentrations correspond to lower glutaraldehyde concentrations and lower salt concentrations correspond to higher glutaraldehyde concentrations.

* * * * *